(12) United States Patent
Sannicolo' et al.

(10) Patent No.: US 7,307,037 B2
(45) Date of Patent: Dec. 11, 2007

(54) METALLIC CATALYSTS FOR CHEMO-, REGIO- AND STEREOSELECTIVE REACTIONS, AND CORRESPONDING PRECURSORS

(75) Inventors: Francesco Sannicolo', Milan (IT); Oreste Piccolo, Sirtori (IT); Tiziana Benincori, Milan (IT); Mara Sada, Rho (IT); Alessandra Verrazzani, Pisa (IT); Simona Tollis, Sora (IT); Elio Ullucci, Latina (IT); Lorenzo De Ferra, Rome (IT); Simona Rizzo, San Giuliano Milanese (IT)

(73) Assignee: Chemi S.p.A., Cinisello Balsamo (IT)

( * ) Notice: Subject to any disclaimer, the term of this patent is extended or adjusted under 35 U.S.C. 154(b) by 525 days.

(21) Appl. No.: 10/506,305

(22) PCT Filed: Mar. 3, 2003

(86) PCT No.: PCT/EP03/02160

§ 371 (c)(1),
(2), (4) Date: Sep. 1, 2004

(87) PCT Pub. No.: WO03/074169

PCT Pub. Date: Sep. 12, 2003

(65) Prior Publication Data

US 2005/0107248 A1    May 19, 2005

(30) Foreign Application Priority Data

Mar. 1, 2002    (IT) .......................... MI2002A0415

(51) Int. Cl.
*B01J 31/00* (2006.01)
*C07F 15/00* (2006.01)
*C07F 9/547* (2006.01)
*C07D 333/00* (2006.01)
*C07D 209/00* (2006.01)

(52) U.S. Cl. ...................... 502/162; 548/402; 548/412; 549/3; 549/6

(58) Field of Classification Search ................ 548/402, 548/412; 549/3, 6; 502/162
See application file for complete search history.

(56) References Cited

U.S. PATENT DOCUMENTS 5,329,015 A    7/1994    Burk ........................... 549/10

FOREIGN PATENT DOCUMENTS

| WO | WO 99/24444 | 5/1999 |
| WO | WO 03/031456 A2 | 4/2003 |
| WO | WO 03/074160 A3 | 9/2003 |

OTHER PUBLICATIONS

Fernandez et al., "Rationally Designed Improvement of the Bis(phospholano)ethane Ligand for Asymmetric Hydrogenation Leads to Reappraisal of the Factors Governing the Enantioselectivity of Duphos Catalysts," Chem. Commun. 17:1663-1664, 2000.

*Primary Examiner*—Porfirio Nazario-Gonzalez
(74) *Attorney, Agent, or Firm*—Clark & Elbing LLP

(57) ABSTRACT

Metallic catalysts of the general formula (I) and their precursors, suitable for chemo- regio- and stereoselective reactions, derived from ortho-bis-(1-phospholanyl)-heteroarenes. The new catalysts are characterized by the presence of two homo-morphic phospholanic rings set in adjacent positions of an aromatic pentatomic heterocycle

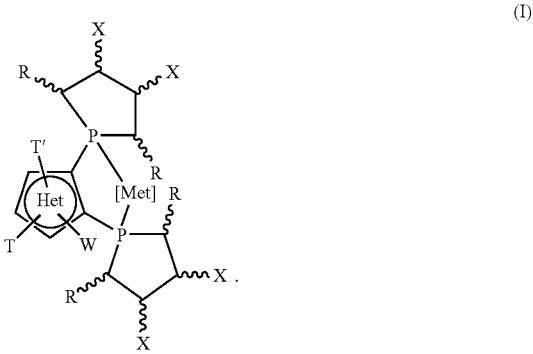

(I)

28 Claims, No Drawings

METALLIC CATALYSTS FOR CHEMO-, REGIO- AND STEREOSELECTIVE REACTIONS, AND CORRESPONDING PRECURSORS

This application is a national stage application under 35 U.S.C § 371 of, and claims priority from, PCT/EP03/02160, filed on Mar. 3, 2003, which claims priority from Italian Patent Application No. MI2002A000415, filed on Mar. 1, 2002.

FIELD OF THE INVENTION

The invention relates to new metallic catalysts and their precursors, characterized by the presence of ortho-bis(1-phospholanyl)heteroarenes, of the general formula (I), suitable for chemo- regio- and stereoselective reactions.

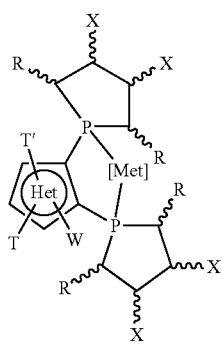

(I)

where:

[Met] is a metal chosen from the group consisting of Ru, Rh, Ir, Pt, Pd, Ni, Re, and Cu having a number of oxidation n, where n is 0, +1, +2 or +3, and containing possible ancillary co-ligands for completing its state of valence;

represents an aromatic pentatomic heterocycle, containing at least one hetero-atom selected from oxygen, sulphur and nitrogen;

T and T', which are the same as or different from one another, are selected from hydrogen, a linear, cyclic or branched C1-C10 alkyl, hydroxyalkyl, alkoxyalkyl, phenyl, alkylphenyl, naphthyl, alkoxyphenyl, dialkylaminophenyl, carboxyphenyl, carbalkoxyphenyl, or else T and T', taken together, constitute an aromatic carbocyclic ring, which is possibly substituted by one or more alkyl, hydroxy, alkoxy, dialkylamino, carboxy, carbalkoxy or sulphonic groups;

W is a substituent present only when the hetero-atom is nitrogen and is selected from H, a linear, cyclic, or branched C1-C10 alkyl, alkoxyalkyl, phenyl, alkylphenyl, naphthyl, alkoxyphenyl, dialkylaminophenyl, carboxyphenyl, carbalkoxyphenyl;

R is selected from hydrogen, a linear, cyclic or branched C1-C10 alkyl, hydroxyalkyl, alkoxyalkyl, phenyl, alkylphenyl;

X is selected from H, a linear, cyclic or branched C1-C10 alkyl, hydroxy, alkoxy, benzyloxy, acyloxy, O-tetrahydropyranyl, O-tetrahydrofuranyl, or else where the two substituents X, taken together with m carbon atoms bound thereto, with m=1, 2 or 3, form a carbocyclic ring with a total of 5-7 atoms or a saturated heterocyclic ring with 5-7 atoms.

In the case of stereogenic carbon atoms present in the phospholanic ring, in the general formula (I) there are to be understood as included the meso products, the racemic products, and the enantiomerically enriched products, with the limitation, in the case of optically active products, that:

a) the carbon atoms in positions 2' and 5' of the phospholanic rings possess the same absolute configuration with respect to one another;

b) the carbon atoms in positions 3' and 4' of the phospholanic rings possess the same absolute configuration with respect to one another;

The said metallic catalysts are useful in chemo- regio- and stereoselective reactions of hydrogenation, reduction, isomerization, and in reactions of formation of C—C bonds. In particular, as regards the reactions of asymmetrical synthesis, the new catalysts prove particularly useful and efficient in enantioselective reactions of hydrogenation of C=C, C=O, C=N groups, of isomerization of enamines, of formation of C—C bonds, such as, for example, the Heck reaction, the Diels-Alder reaction, allylic substitution and aldolic condensation.

STATE OF THE ART

A large number of chelating phosphine ligands has been prepared in the last 30 years, and described in patent literature and in scientific publications, as fundamental component of metallic complexes, useful as catalysts for chemo-, regio- and enantioselective reactions. [c.f., for example, H. Brunner, W. Zettimeier, "Handbook of enantioselective catalysis", VCH, (1993) or I. Ojima ed., "Catalytic Asymmetric Synthesis", Wiley, (2000)]. The concept is, however, commonly and universally accepted that there does not exist a catalyst, and hence a ligand, suitable for every reaction and for every substrate. There thus remains felt the need, in particular for applications of industrial interest, to identify new catalysts suitable both for previously unknown reactions and for improving the results of existing reactions.

In particular, the modern design of new catalysts provided with high capacities of stereoselection tends, more than in the direction of the creation of a single catalyst, even a very efficient one, in the direction of the identification of a modular class of catalysts, i.e., ones provided with a modifiable basic architecture, both in the steric properties and in the electronic properties according to the needs imposed by the reaction and by the substrate.

The former of these two parameters plays a predominant role in regulating the capacity of stereoselection of the catalyst, whilst the latter has a decisive influence on the kinetics of the catalytic process.

The publications and the patents of catalysts containing phosphinic ligands with a phospholanic structure, such as, for example, the documents U.S. Pat. No. 5,171,892, U.S. Pat. No. 5,329,015, U.S. Pat. No. 6,043,396, WO 99/24444, WO 00/11008, have demonstrated the usefulness of such a substructure containing a phosphacycle. However, the limit of such systems is the difficulty of modulating the steric and electronic properties, given that what links the two phospholanic systems (the linker) is an aromatic carbocycle, an alkyl chain or a ferrocenic system. Consequently, the linker not only imposes and imparts a large part of the characteristics of the angles of valence with the metal (the so-called "bite angle") in the metal complex, but contributes to an important extent to the determination of its electronic properties. A further limit is represented by the fact that it is possible to have systems where the two phosphorus atoms are homotopic (ligands with $C_2$ symmetry), whilst it is known that, in some reactions, metallic catalysts deriving from ligands with $C_1$ symmetry are more efficient [I. Ojima ed., "Catalytic Asymmetric Synthesis", Wiley, (2000)]. The aforesaid inventors, according to the authors of the present patent application, have apparently underestimated the importance of the linker, even though, in actual fact, the results observed in numerous and different reactions and on substrates having different steric and electronic characteristics demonstrate the significant role played by the bite angle, and by the structural flexibility of the catalytic system, which can substantially be ascribable to what links the two phospholanic systems.

Recently, the present applicant has carried ahead a detailed theoretical and experimental study demonstrating in patents and publications how it is possible to obtain a fine steric and electronic modulation, which is necessary for optimization of chemo- regio- and stereoselective reactions. For instance, in the patent application WO99/52915, there were claimed new ligands with $C_1$ symmetry containing phospholanic rings as substructures and the corresponding metallic catalysts. A limit of this invention is, however, represented by the fact that the phosphacycles illustrated are set at intervals of 4 carbon atoms part, with the consequent impossibility of obtaining bite angles (P-Metal-P), calculated by computer modelling, of less than 90°. In addition, in the said systems there is present a further source of stereogenicity, represented by the atropoisomeric system, which does not necessarily present the same type of asymmetric induction promoted by the phospholanic systems; i.e., it is possible to encounter cases where the atropoisomeric stereogenicity and the stereogenicity of the phosphacyclic ring go in the same direction ("matched stereoselectivity induction"), but also cases where the effects may go in the opposite direction, with an overall reduction in asymmetric induction ("mismatched stereoselectivity induction"). Proceeding in the search for new, simpler and more effective catalytic systems with $C_2$ and $C_1$ symmetry, the present applicant has found the catalysts of the present invention, which, as compared to systems already known, adapt better to the structural and electronic needs of the reagents and of the type of reactions, so enabling the limits of the pre-existing catalytic systems to be overcome. Consequently, the improvement that can be achieved in terms of productivity, and regio-, chemo- and stereoselectivity, makes possible a wider industrial application.

DETAILED DESCRIPTION OF THE INVENTION

The subject of the present invention are new metallic complexes and their precursors, characterized by the presence of ortho-bis(1-phospholanyl)heteroarenes, of the general formula (I), which are suitable for chemo- regio- and stereoselective reactions,

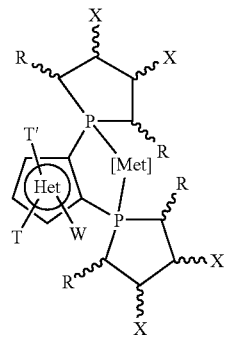

where:

[Met] is a metal chosen from the group consisting of Ru, Rh, Ir, Pt, Pd, Ni, Re, Cu, having a number of oxidation n, where n is 0, +1, +2, or +3, and containing possible ancillary co-ligands for completing its state of valence;

represents an aromatic pentatomic heterocycle, containing at least one hetero-atom selected from oxygen, sulphur, and nitrogen;

T and T', which are the same as or different from one another, are selected from hydrogen, a linear, cyclic or branched C1-C10 alkyl, hydroxyalkyl, alkoxyalkyl, phenyl, alkylphenyl, naphthyl, alkoxyphenyl, dialkylaminophenyl, carboxyphenyl, carbalkoxyphenyl, or else T and T', taken together, constitute an aromatic carbocyclic ring, which is possibly substituted by one or more alkyl, hydroxy, alkoxy, dialkylamino, carboxy, carbalkoxy or sulphonic groups;

W is a substituent present only when the hetero-atom is nitrogen and is selected from H, a linear, cyclic or branched C1-C10 alkyl, alkoxyalkyl, phenyl, alkylphenyl, naphthyl, alkoxyphenyl, dialkylaminophenyl, carboxyphenyl, carbalkoxyphenyl;

R is selected from hydrogen, a linear, cyclic or branched C1-C10 alkyl, hydroxyalkyl, alkoxyalkyl, phenyl, alkylphenyl;

X is selected from H, a linear, cyclic or branched C1-C10 alkyl, hydroxy, alkoxy, benzyloxy, acyloxy, O-tetrahydropyranyl, O-tetrahydrofuranyl, or else where the two substituents X, taken together with m carbon atoms bound thereto, with m=1, 2 or 3, form a carbocyclic ring with a total of 5-7 atoms or a saturated heterocyclic ring with 5-7 atoms.

In the case of stereogenic carbon atoms present in the phospholanic ring, in the general formula (I) there are to be understood as included the meso products, the racemic products, and the enantiomerically enriched products, with the limitation, in the case of optically active products, that:

a) the carbon atoms in positions 2' and 5' of the phospholanic rings possess the same absolute configuration with respect to one another;

b) the carbon atoms in positions 3' and 4' of the phospholanic rings possess the same absolute configuration with respect to one another;

These metallic catalysts are useful in chemo- regio- and stereoselective reactions of hydrogenation, reduction, isomerization and in reactions of formation of C—C bonds. In particular, as regards the reactions of asymmetrical synthesis, the new catalysts prove particularly useful and efficient in enantioselective reactions of hydrogenation of C=C, C=O, C=N groups, of isomerization of enamines, of formation of C—C bonds, such as, for example, the Heck reaction, the Diels-Alder reaction, allylic substitution and aldolic condensation.

The catalysts forming the subject of the present invention are prepared starting from the phospholanic ligands of formula (IA)

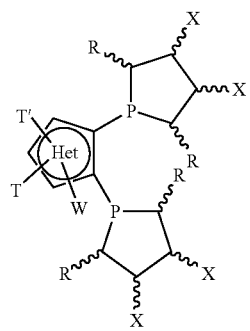

(IA)

in which T, T', W, X and R have the aforesaid meanings.

These ligands, on account of the presence of the hetero-aromatic linker, show electronic properties different from those of the corresponding ligands with a carbocyclic linker. In addition, according to the relative position of the phosphorus atoms with respect to the hetero-atom present in the linker, the electronic density of the two phosphorus atoms may be differentiated from one another.

Also the steric properties of these ligands vary according to the substituents T, T' and W.

It is thus possible to obtain, with these ligands, catalysts that adapt better to the requirements of the reagents and to the type of the reactions, obtaining, in practice an improved catalytic activity, as demonstrated by kinetic measurements.

Purely by way of example, indicated in what follows are the characteristics of some classes of metallic catalysts containing the ligands of structure (II)-(IV), where Y is selected from O, S and N(W), T and W are selected from hydrogen and methyl, and where the carbon atoms in positions 2' and 5' of the phospholanic rings have the same absolute configuration with respect to one another:

a) the catalysts containing the ligands, where T or else W is methyl, have steric hindrance different from those containing ligands where T or else W is hydrogen;

b) the phosphorus atoms of the ligands (II), depending upon the different electronic availability imparted by the heterocycle, when there is present an atom of oxygen, sulphur or else nitrogen, have electronic characteristics that are different from one another, which reflect upon the characteristics of the catalysts that contain them;

c) the ligands (III) contain two phosphorus atoms having different electronic availability;

d) the ligands (IV) offer a further possibility of differentiating the steric and electronic characteristics of the phosphorus atoms.

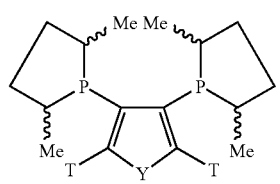

(II)

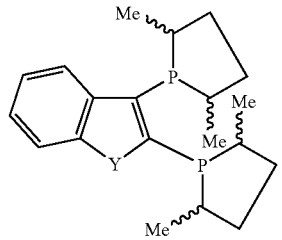

(III)

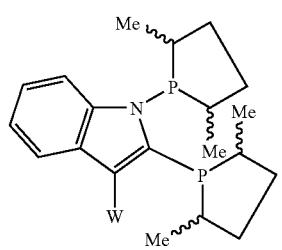

(IV)

These properties (a-d) were hard to obtain or even unobtainable in catalysts containing the phosphacyclic system so far known and enable the previous limitations to be overcome.

The synthesis of the new ligands (IA) uses reaction schemes in themselves known [c.f., for instance, H. Brunner et al., J. Organomet. Chem. 328, 71 (1987); M. J. Burk, J. Am. Chem. Soc., 113, 8518 (1991); M. J. Burk et al., Organometallics 9, 2653 (1990); M. J. Burk, J. Am. Chem. Soc., 115, 10125 (1993); J. Holz et al J. Org. Chem., 63, 8031 (1998), Y.-Y. Yan and T. V. RajanBabu, J. Org. Chem., 65, 900 (2000)]. For instance, purely by way of example, some of these ligands may be prepared according to Schemes 1 and 1' (in both schemes, Hal is a halogen atom, and G and G' are a mesylate group, a tosylate group or, taken together, represent the group O—SO$_2$—O).

In particular, the first reaction of both schemes is a halogenation of the hetero-aromatic ring in positions 3 and 4 or else 2 and 3, respectively. Subsequently, the heteroarene dihalogen can be reacted with a phospholane in the presence of palladium-based catalysts to obtain the desired product.

Alternatively, the heteroarene dihalogen can be reacted with triethyl phosphite to obtain the corresponding bis-diethoxyphosphoryl heteroarene, which is subsequently reduced with lithium aluminium hydride to bis-diphosphinoheteroarene. Finally, the latter is reacted with bifunctional alkylating agents derived from the 2,4-hexanediol, such as, for example, the bis-methane sulphonates, the bis-toluene sulphonates or else with cyclic sulphates, to obtain the desired product. In particular, to obtain a phospholanic ligand in a specific enantiomeric form, it is necessary for the reagents used to have the two stereocentres with the same absolute configuration.

Scheme 1

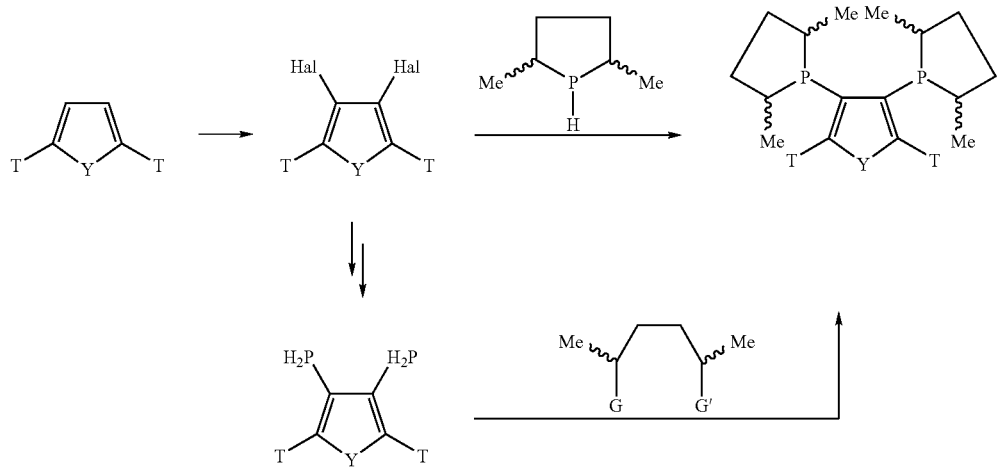

Scheme 1'

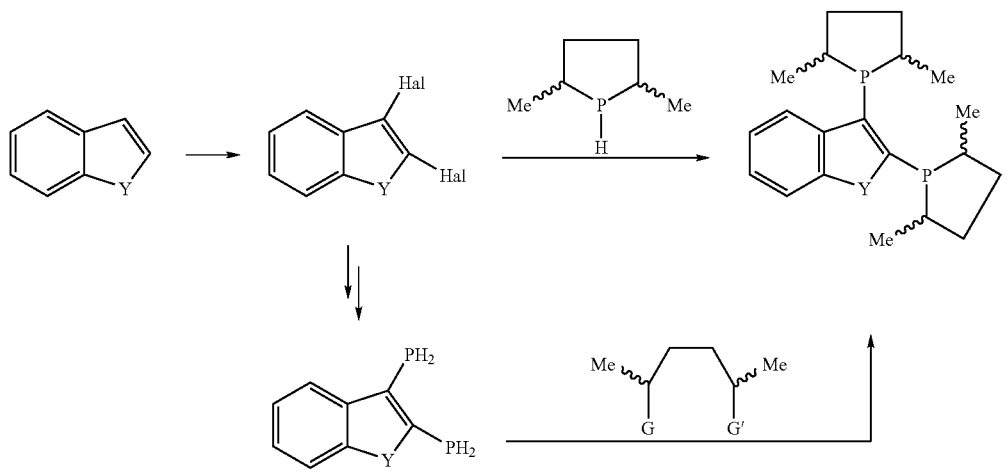

The preparation of the catalysts of formula (I) is conducted using the phospholanic ligands of formula (IA), according to methodologies known to the person skilled in the art [c.f., for example T. G. Schenck et al., Inorg. Chem. 24, 2334 (1985); and K. Mashima et al., J. Org. Chem., 59, 3064 (1994)]. Shown in Scheme 2, purely by way of example, are the synthetic schemes of some catalysts of formula (I) according to the present invention.

-continued

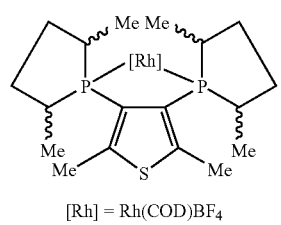

[Rh] = Rh(COD)BF$_4$

Schema 2

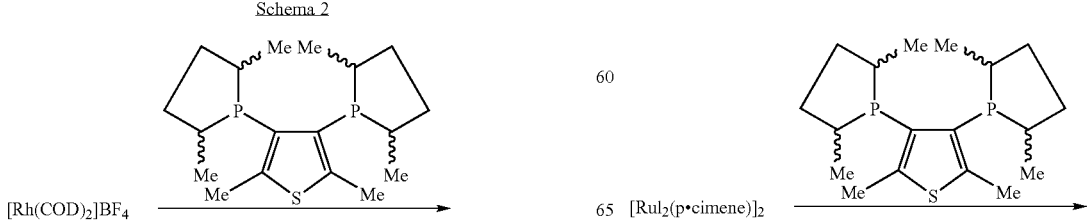

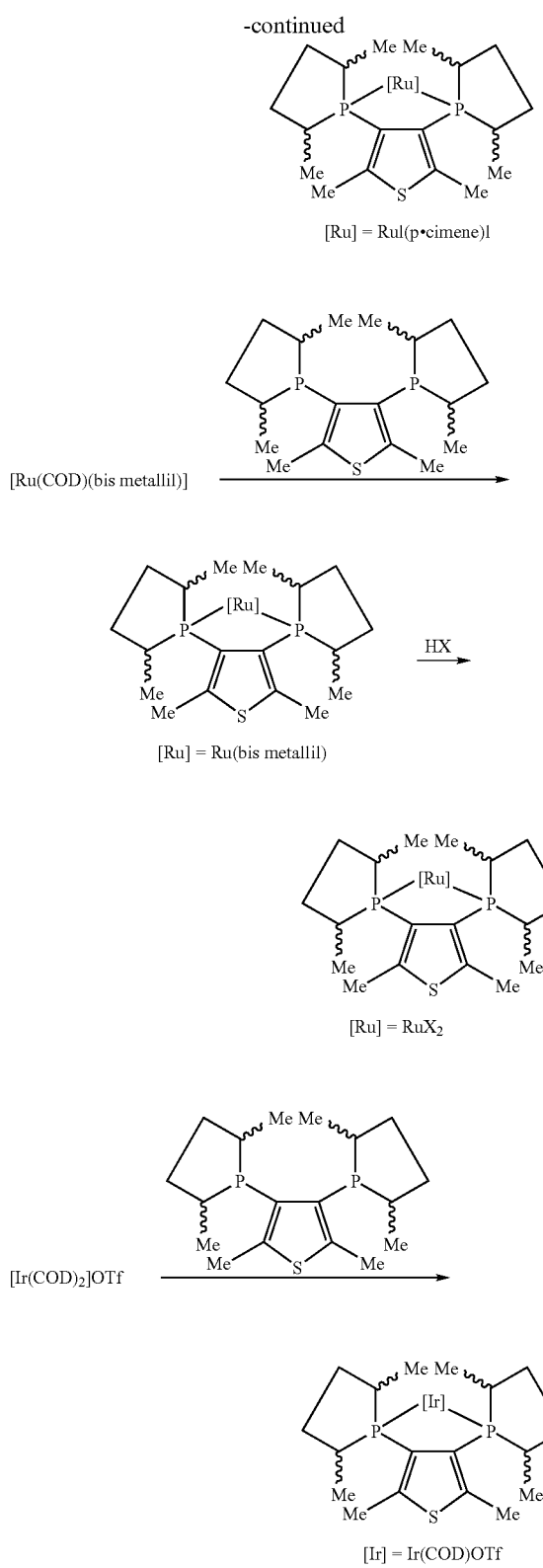

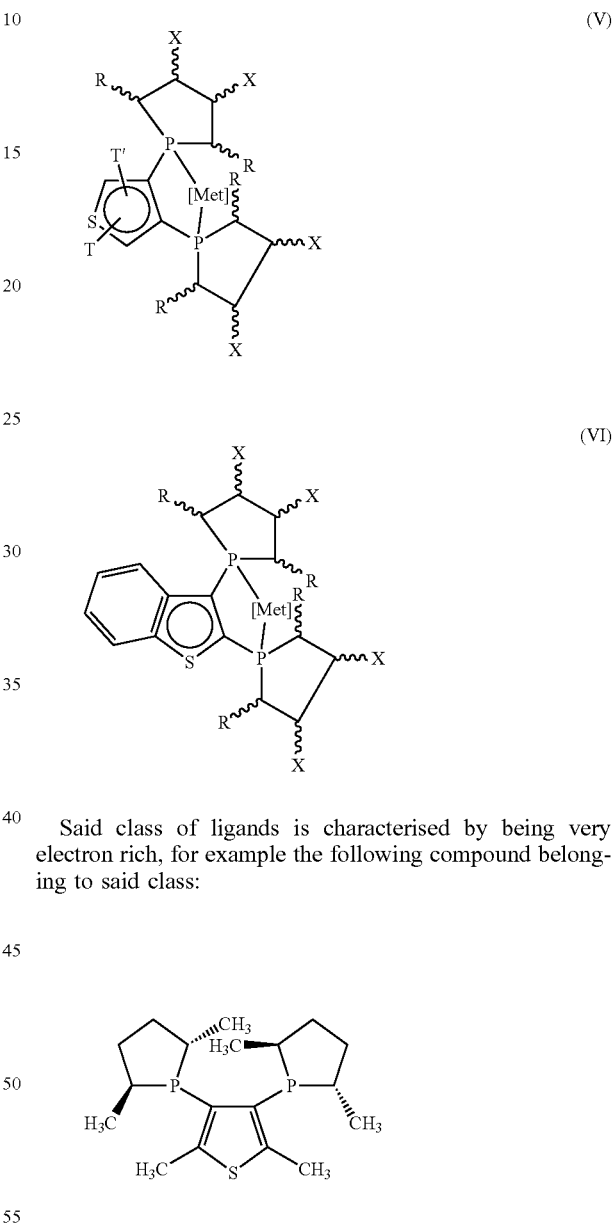

such as, for example, the Heck reaction, the Diels-Alder reaction, allylic substitution and aldolic condensation.

Amongst the metallic catalysts based on Rh, Ru, Ir, Pd, Pt, Re, Ni or Cu, of the general formula (I), there are preferentially selected those containing a thiophenic or benzothiophenic ring of the general formula (V) and (VI), respectively.

Said class of ligands is characterised by being very electron rich, for example the following compound belonging to said class:

has an oxidation potential equal to 0.1V.

Further preferred are the metallic catalysts of formula (V) and (VI), where T and T' are both hydrogen or both methyl, where R is other than hydrogen, and the two stereocentres present in positions 2' and 5' of the pholpholanic rings have, with respect to one another, the same absolute configuration, and where the two stereocentres in positions 3' and 4' of the phospholanic rings, if present, have, with respect to one another, the same absolute configuration.

The catalysts forming the subject of the present invention have advantageously been applied in regio-, chemo- and stereoselective reactions and in particular in enantioselective reactions of hydrogenation of C=C, C=O, C=N groups, of isomerization of enamines, of formation of C—C bonds, An other preferred class of metallic catalysts according to the present invention is the following of formula (VII)

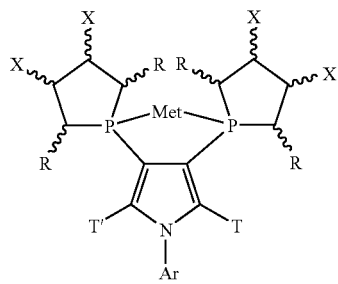
(VII)

wherein T and T' preferably are both H or both the same linear, cyclic or branched C1-C10 alkyl, R is CH$_3$, Ar is an electron donor aryl residue. For electron donor aryl group, we mean a phenyl group, or an aryl residue substituted with electron donor groups.

This complex is prepared by using the class of ligands having the general formula (VIIA)

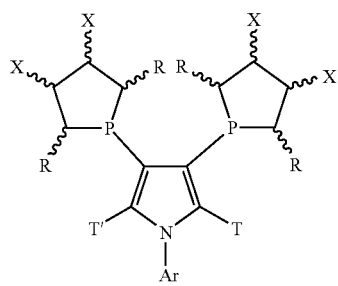
(VIIA)

wherein T, T', R, X and Ar have the aforesaid meanings.

Said class of ligands is characterised by being very electron rich, for example the following compound belonging to said class:

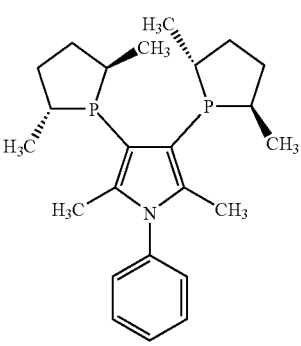

has an oxidation potential equal to 0.2V.

The considerably high electronic supply of the donor atoms of the ligand in the complex is a very important requisite in order to obtain valuable kinetics in the hydrogenation reactions of the double bonds C=C and C=O.

The aforesaid class of ligands (VIIA) and in particular the aforesaid compound is also very interesting since it can be prepared very easily, since it is possible to obtain the contemporaneous insertion of the two adjacent phosphorus atoms in a single step as it results from the following scheme 3 by reacting 1-phenyl-2,5-dimethylpyrrole with an excess of PBr$_3$ according to a typical and conventional reaction for the pyrrole ring.

Scheme 3

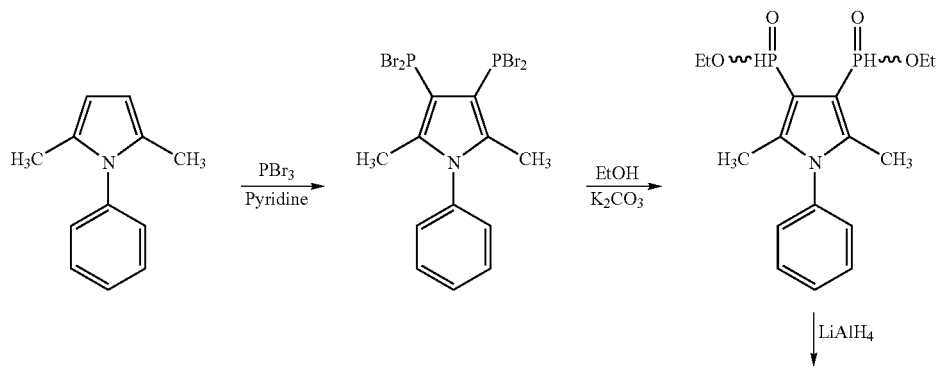

-continued

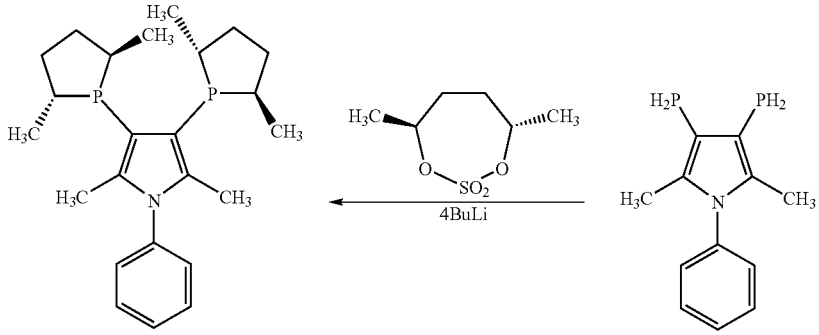

As illustration of the present invention the following non-limiting examples are provided.

EXAMPLE 1

Synthesis of (R,R) 2,5-dimethyl-[3,4-bis(2',5'-dimethylphospholanyl)]-thiophene

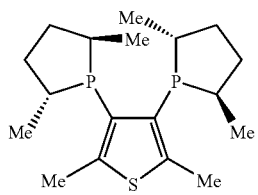

Stage a: Synthesis of 2,5-dimethyl-3,4-diiodo-thiophene

Into a 2-L four-necked flask, provided with mechanical stirrer, thermometer and reflux condenser, there were introduced 80 mL of $H_2O$, 20 g of $NaIO_3$, 26 g of $I_2$, 7 mL of AcOH, 60 g of 3-iodo-2,5-dimethylthiophene, dissolved in 600 mL of AcOEt and 6 mL of $H_2SO_4$.

The solution was brought to approximately 77° C. and left under stirring for 18 hours.

The solution was then washed with two 300-mL portions of brine, with two portions of $Na_2S_2O_3$ solution for removing the oxidant excess ($H_2O$ 100 mL, $Na_2S_2O_3$ 5 g, NaOH 5 g), with a 300-mL portion of a saturated aqueous solution of $NaHCO_3$, and again with a 300-mL portion of brine.

The organic phase was evaporated, recovering a red-coloured solid residue. The solid was then washed with two 80-mL portions of MeOH, to obtain, with this procedure, 75 g of product 2,5-dimethyl-3,4-diiodo-thiophene (yield 82%).

Stage b: Synthesis of 2,5 dimethyl-3,4-bis(diethoxyphosphoryl)-thiophene

Into a 500-mL four-necked flask, provided with magnetic stirrer, thermometer, dropping funnel and distillation apparatus, there were introduced, under a nitrogen atmosphere, 9.86 g of palladium acetate and 200 mL of $P(OEt)_3$.

To the solution, brought to 140° C., there were added dropwise, in approximately 2 hours, 40 g of 2,5-dimethyl-3,4-diiodo-thiophene, dissolved in 150 mL of $P(OEt)_3$. The solution was left under stirring at 140° C. for a further 3 hours, and then the solvent was evaporated in vacuo (46-105° C.; 4 mmHg).

The oily residue was extracted with five 100-mL portions of heptane, and the extracts were combined and evaporated. There was obtained an oil, which was further purified by chromatography on silica gel. (eluent AcOEt/EtOH 9/1). In this way, there were recovered 20 g of 2,5-dimethyl-3,4-bis(diethoxyphosphoryl)-thiophene (yield 48%). A sample was purified by distillation [boiling point=170-175° C./3 torr (4 mbar)].

$^1$H-NMR: 4.15 ppm (m, 8H); 2.6 ppm (d, 6H); 1.3 ppm (t, 12H). $^{31}$P-NMR: 12.5 ppm The pure product was a colourless solid that crystallized from pentane Stage c: Synthesis of 2,5-dimethyl-3,4-bis(diphosphino)-thiophene Into a 250-mL four-necked flask, provided with magnetic stirrer, thermometer and dropping funnel, there were introduced, under a nitrogen atmosphere, 3.6 g of $LiAlH_4$ and 80 mL of dry THF.

The solution was brought to −60° C. and 11.2 mL of $(CH_3)_3SiCl$ were added by means of a syringe. The suspension was then left under stirring for 2 hours at room temperature.

The mixture was cooled again to −60° C., and there were dropped, in 20 minutes approximately, 5.6 g of 2,5-dimethyl-3,4-bis(diethoxyphosphoryl)-thiophene dissolved in 20 mL of THF, and the solution was left under stirring at room temperature for 3 hours.

There were then added to the mixture, in the following order, 3.6 mL of $H_2O$, 3.6 mL of 1.5% NaOH, and again 10.8 mL of $H_2O$, and the mixture was then left under stirring up to the formation of a filterable precipitate.

After filtration, the precipitate was washed with four 20-mL portions of THF, and the solvent was evaporated.

The residue was dissolved in 50 mL of toluene and washed with two 20-mL portions of $H_2O$. The organic phase was filtered on decalite and evaporated, to obtain with this procedure 2.5 g of crude 2,5-dimethyl-3,4-bis(diphosphino)-thiophene (yield>90%). A sample of product was purified by distillation [boiling point: 70-75° C./5 torr (6.7 mbar)].

$^1$H-NMR: 4.2 ppm (t, 2H); 3.2 ppm (t, 2H); 2.5 ppm (s, 6H). $^{31}$P-NMR: −155 ppm The pure product is a colourless liquid.

Stage d: Synthesis of (R,R) 2,5-dimethyl-[3,4-bis (2',5'-dimethylphospholanyl)]-thiophene)

Into a 250-mL four-necked flask, provided with magnetic stirrer, thermometer and dropping funnel, there were introduced, under a nitrogen atmosphere, 0.47 g of 2,5-dimethyl-3,4-bis(diphosphino)-thiophene, 0.96 g of (S,S) 4,7-dimethyl-[1,3,2]dioxathiepane-2,2-dioxido, and 30 mL of dry THF.

The solution was brought to 10° C., and 7.5 mL of nBuLi (1.7 M) were added, in approximately 40 minutes, by means of a syringe. The mixture was then left under stirring for 60 minutes at 10° C., and there were then added 2.5 mL of methanol. The solution was filtered, evaporated, and extracted with three 20-mL portions of heptane. The organic phases were combined, filtered and evaporated, and the residue was washed with two 3-mL portions of MeOH.

With this procedure, there were recovered 0.46 g of (R,R) 2,5-dimethyl-[3,4-bis(2',5'-dimethylphospholanyl)]-thiophene) (yield 50%).

$^1$H-NMR: 0.94 ppm (m, 6H, —CH$_3$); 1.17 ppm (m, 6H, —CH$_3$); 1.25-1.55 ppm (m, 4H); 2.0-2.2 ppm (m, 4H); 2.46 ppm (s, 6H, —CH$_3$); 2.4-2.6 ppm (m, 2H); 3.0-3.1 ppm (m, 2H). $^{31}$P-NMR: 4.1 ppm (s). Mass (M$^+$): 340 [α]$^{25}_D$+54.2 (c=1, chloroform) redox potential (E°): 0.1 V

EXAMPLE 2

Synthesis of (R,R) [3,4-bis(2',5'-dimethylphospholanyl)]-thiophene

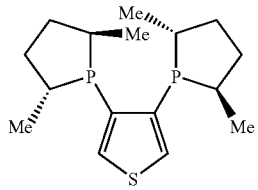

Stage a: Synthesis of 3,4-dibromo-thiophene

Br$_2$ (23.5 mL) was dropped into a solution of thiophene (31.6 g) in CHCl$_3$ (38 mL), at a temperature of 0° C. under stirring, within an interval of 1 h 30 min. Next, Br$_2$ (10 mL) was added at room temperature. The mixture was heated under reflux for 3 h 30 min, and then NaOH 2N (57 mL) was added with caution, and the heating was prolonged for a further 30 min. The mixture was poured into a beaker and cooled to room temperature. The solid was collected by filtration and washed with abundant water. After crystallization from CHCl$_3$, there were obtained 134.6 g of 2,3,4,5-tetrabromothiophene, which were slowly added in portions to a mixture, under stirring at 50° C., of 400 mL of H$_2$O, 107 g of powdered zinc and 600 mL of AcOH. The solution was left under stirring at a temperature of approximately 60° C. for 45 min and at room temperature for 12 h. The solution was diluted with water and extracted with CH$_2$Cl$_2$. The organic phase was washed with a saturated solution of NaHCO$_3$, with H$_2$O, and then dehydrated on Na$_2$SO$_4$. The solvent was evaporated, and the residue was distilled at reduced pressure [boiling point: 104-107° C., 22.5 torr (30 mbar)] to yield 3,4-dibromo-thiophene (53.5 g) (yield 54%).

Stage b: Synthesis of 3,4-bis(diethoxyphosphoryl)-thiophene

A suspension of PdCl$_2$ (0.15 g) in 3,4-dibromo-thiophene (2.0 g) was brought to the temperature of 115° C., and P(OEt)$_3$ (3.3 g) was then dropped under stirring, in an inert atmosphere, bringing the temperature of the bath to 130° C. Once dropping was completed, the clear yellow solution was heated to 160° C. for 1 h 30 min. The mixture was diluted with CH$_2$Cl$_2$, washed twice with water, dehydrated, and the solvent was evaporated at reduced pressure. The residue underwent chromatography on silica gel by flash chromatography (AcOEt). The tail fractions (Rf: 0.15) were collected, evaporated at reduced pressure to yield an oil, which was distilled under vacuum conditions in bubble apparatus [boiling point=210° C./0.5 torr (0.73 mbar)] to yield the 3,4-bis(diethoxyphosphoryl3-thiophene (1.3 g) as yellowish oil, which solidified at low temperature (yield 54%)

m.p.: 28-30° C.; $^1$H-NMR: 1.2 ppm (m, 12H); 4.1 ppm (m, 8H); 8.1 ppm (m, 2H). $^{31}$P-NMR: 11 ppm (s); $^{13}$C-NMR: 16 ppm (CH$_3$); 62 ppm (CH$_2$); Mass (M$^+$): 356.

Stage c: Synthesis of 3.4-bis(diphosphino)-thiophene

Trimethyl chlorosilane (0.94 mL) was added, under an inert atmosphere, to a suspension of LiAlH$_4$ in THF (7.4 mL, 1 M) at the temperature of −78° C. and was left under stirring for 2 h at room temperature. The solution was then brought to the temperature of −60° C., and there was dropped a solution of 3,4-diethylphosphonate (0.44 g) in THF (7.4 mL), and it was then left under stirring at room temperature for 2 h. The reaction was exhausted with MeOH (2.5 mL), cooling with an ice bath. The solvent was evaporated at reduced pressure, and the grey solid obtained was washed with degassed CH$_2$Cl$_2$ (approximately 15 mL). By evaporation of the solvent, a yellowish residue was obtained, which was distilled in a bubble apparatus under vacuum conditions [boiling point=80-90° C. 0.2 torr (0.27 mbar)], eliminating some low-boiling top fractions (boiling point=50° C.); 3,4-bis(diphosphino)-thiophene was obtained as a colourless oil, which was kept under argon at −10° C.

TLC: Rf=0.5 (hexane); $^1$H-NMR: 3.6-4.2 ppm (d, 4H); 7.5 ppm (m, 2H); $^{31}$P-NMR: −148 ppm (s)

Stage d: Synthesis of (R,R) 3,4-bis(2',5'-dimethylphospholanyl)-thiophene

Into a three-necked flask provided with magnetic stirrer, there were introduced, in a nitrogen atmosphere, 20.3 mg of 3,4-bis(diphosphino)-thiophene, 50 mg of (S,S) 4,7-dimethyl-[1,3,2]dioxathiepane-2,2-dioxide and 4 mL of THF. The solution was brought to 10° C., and 0.38 mL of nBuLi (1.6 M) were added in approximately 15 minutes by means of a syringe; the mixture was then left under stirring overnight. Then, the reaction was exhausted with 1 mL MeOH; after evaporation of the solvent, the residue was washed with two portions of MeOH, the solvent was again evaporated, and the solid obtained was washed with 10 mL of CH$_2$Cl$_2$. The oily residue, recovered by evaporation of the solvent at reduced pressure, underwent chromatography on silica gel (CH$_2$Cl$_2$-EtOH), to obtain 30 mg of (R,R) 3,4-bis(2',5'-dimethylphospholanyl)-thiophene.

$^1$H-NMR: 0.75 ppm (m, 6H, —CH$_3$); 1.22 ppm (m, 6H, —CH$_3$); 1.20-1.35 ppm (m, 4H); 1.8-2.1 ppm (m, 4H); 3.4 ppm (m, 2H); 7.5 ppm (m, 2H aromatic); $^{31}$P-NMR: 13.1 ppm (s).

EXAMPLE 3

Synthesis of (R,R) [3,4-bis(2',5'-dimethylphospholanyl)]-benzo[b]thiophene

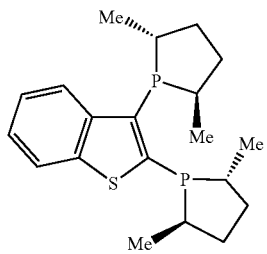

Stage a: Synthesis of 2,3-dibromo-benzo[b]thiophene

A solution of $Br_2$ (21.1 mL) in $CHCl_3$ (65 mL) was dropped into a solution of benzo[b]thiophene (26.4 g) in $CHCl_3$ (120 mL), under stirring, at a temperature of 0° C. The progress of the reaction was controlled in TLC (hexane) up to the disappearance of the starting product: Rf (thianaphthene): 0.33, Rf (2,3-dibromobenzothiophene): 0.5. The mixture was then poured into aqueous, NaOH; the organic phase was separated, washed twice with a solution of 10% NaOH and once with water, and then dehydrated on $Na_2SO_4$. The solvent was evaporated to yield the 2,3-dibromo-benzo[b]thiophene as a white solid (52 g) (yield 90%).

Stage b: Synthesis of 2,3-bis(diethoxyphosphoryl)-benzo[b]thiophene

A suspension of $PdCl_2$ (0.15 g) in 2,3-dibromothianaphthene (2.4 g) was brought to the temperature of 115° C., and $P(OEt)_3$ (3.3 g) was then dropped under stirring and in an inert atmosphere. Once dropping was completed, the red solution was brought to 160° C. After 1 h 30 min, the mixture was diluted with $CH_2Cl_2$, washed twice with water and dehydrated. The solvent was evaporated at reduced pressure to yield a residue that underwent chromatography on silica gel by flash chromatography (AcOEt), to yield 2,3-bis(diethoxyphosphoryl)-benzo[b]thiophene (1.6 g) (yield 60%).

m.p.: 67° C.; $^1$H-NMR: 1.4 ppm (m, 12H); 4.2 ppm (m, 8H); 7.4 ppm (m, 2H); 7.85 ppm (m, 1H); 8.5 ppm (m, 1H); $^{31}$P-NMR: 9.0 ppm 9.6 ppm

Stage c: Synthesis of 2.3-bis(phosphino)-benzo[b]thiophene

Trimethyl chlorosilane (0.94 mL) was added, in an inert atmosphere, to a suspension of $LiAlH_4$ in THF (7.43 mL, 1 M) at a temperature of −78° C. and was left under stirring for 2 h at room temperature. The solution was then brought to a temperature of −60° C., and a solution of 3,4-diethylphosphonate (0.5 g) in THF (7.43 mL) was dropped, and it was left under stirring at room temperature for 2 h. The reaction was exhausted with MeOH (2.5 mL), cooling with an ice bath.

The solvent was evaporated at reduced pressure, and the grey solid obtained was washed with degassed $CH_2Cl_2$ (approximately 15 mL). By evaporation of the solvent, a yellowish oil was obtained, which underwent chromatography on silica gel in an inert atmosphere (Rf: 0.6, hexane). The 2,3-bis(phosphino)-benzo[b]thiophene obtained as solid, after evaporation of the solvent, was kept under argon at −20° C.

$^1$H-NMR: 3.6 ppm (s, 2H-P); 4.7 ppm (s, 2H-P); 7.4 ppm (m, 2H); 7.9 ppm (m, 2H);

Stage d: Synthesis of (R,R)3,4-bis(2',5'-dimethylphoslholanyl)benzo[b]thiophene A 1.6 M solution in hexane of BuLi (0.12 mL) was dropped into a solution of diphosphine (18 mg) in THF (1.6 mL), and the (orange) solution was left under stirring for 1 h 30 min. There were then dropped 33.2 mg of cyclic sulphate of (2S,5S)-hexanediol dissolved in 2 ml of THF, and the solution turned pale yellow. It was left under stirring for 2 h. A 1.6 M solution in n.hexane of BuLi (0.13 mL) was dropped to carry out the closure of the phospholanic ring, and the solution once again became orange.

After leaving the mixture under stirring for 2 h, the disappearance of the starting product was controlled in TLC (hexane), and the disappearance of the cyclic sulphate was controlled in TLC (AcOEt). The mixture was left under stirring overnight in an inert atmosphere; then the reaction was exhausted with MeOH (0.5 mL), and the solvent was evaporated at reduced pressure. The solid was washed with degassed $CH_2Cl_2$, and the filtrate was concentrated at, reduced pressure. A solid was obtained, which underwent chromatography on silica gel (EtOH). By evaporating the solvent, the product was obtained as a pale-yellow solid.

melting point: 174° C. $^1$H-NMR: 0.75 ppm (m, 6H, —$CH_3$); 1.22 ppm (m, 6H, —$CH_3$); 1.20-1.35 ppm (m, 4H); 1.8-2.1 ppm (m, 4H); 3.7 (m, 4H); 7.3 ppm (m, 4H aromatic). Mass (M$^+$): 362. $[\alpha]^{25}_D$ +24.8 (c=1.39, methylene chloride) redox potential (E°): $P_1$ 0.4 V; $P_2$ 0.65 V

EXAMPLE 4

Preparation of the Complex {Rh(COD) (R,R) 2,5-dimethyl-[3,4-bis(2',5'-dimethylphospholanyl)]-thiophene}BF$_4$

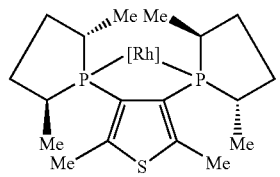

[Rh] = Rh(COD)BF$_4$

A mixture of 96.7 mg of [Rh(COD)$_2$]BF$_4$ prepared according to Inorg. Chem. 24, 2334 (1985) and 90 mg of (R,R) 2,5-dimethyl-[3,4-bis(2',5'-dimethylphospholanyl)]-thiophene, prepared according to Example 1, in 10 mL of degassed methylene chloride was kept under stirring at room temperature for 2 h. The mixture was then added with 5 mL of degassed THF, and then slowly 10 mL of degassed hexane, subsequently concentrated up to start of crystallization and then kept at −20° C. overnight. The dark-red solid was filtered, washed twice with 3 mL of hexane, and finally dried under vacuum. There were obtained 32.5 mg of catalyst. A further 120 mg, of comparable chemical purity on the basis of the NMR spectra, were recovered by concentration from the mother liquor.

31P-NMR: 51 ppm (d, J=160.5 Hz).

EXAMPLE 5

Preparation of the Complex {Rh(COD) (R,R) 2,5-dimethyl-[3,4-bis(2',5'-dimethylphospholanyl)]-thiophene} OTf

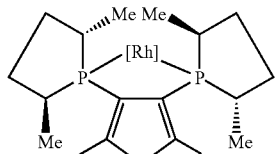

[Rh] = Rh(COD)OTf

A mixture of 108.9 mg of [Rh(COD)$_2$]OTf, prepared according to Inorg. Chem. 24, 2334 (1985) and 88 mg of (R,R) 2,5-dimethyl-[3,4-bis(2',5'-dimethylphospholanyl)]-thiophene, prepared according to Example 1, in 10 mL of degassed methylene chloride was kept under stirring at room temperature for 2 h. The mixture was concentrated up to approximately 40% of the initial volume, and 6 mL of degassed THF and of 4 mL of degassed hexane were added, up to start of crystallization, and it was then kept at −5/−10° C. for 30 min. The orange-red solid was filtered, washed three times with 4 mL of hexane, and finally dried under vacuum Approximately 100 mg of catalyst were obtained.

EXAMPLE 6

Preparation of the Complex {Ru I(p. cymene) (R,R) 2,5-dimethyl-[3,4-bis(2',5'-dimethylphospholanyl)]-thiophene} I

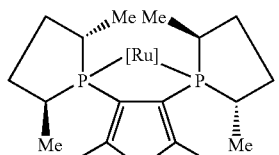

[Ru] = RuI(p·cimene)I

In a four-necked 100-mL flask, provided with a reflux condenser, valve for nitrogen, and magnetic stirrer, there were introduced under nitrogen flow, 144 mg of [RuI$_2$(p.cym)]$_2$ and 100 mg of (R,R) 2,5-dimethyl-[3,4-bis(2',5'-dimethylphospholanyl)]-thiophene, prepared according to Example 1. There were then added 25 mL of CH$_2$Cl$_2$ and 9 mL of degassed MeOH, and the solution was refluxed for two hours. The solvent was evaporated, recovering as residue the catalyst as consisting of a dark-red crystalline solid.

31P-NMR: 79.3 ppm (d, J=45.8 Hz); 59.9 ppm (d, J=45.8 Hz).

EXAMPLE 7

Hydrogenation of N-Acetamido Cinnamic Acid—Comparison of the Catalytic Activity {Rh(COD) (R,R) 2,5-dimethyl-[3,4-bis (2',5'-dimethylphospholanyl)]-thiophene} OTf vs {Rh(COD) [1,2-bis ((2R,5R)-2,5-dimethylpholane)-benzene]}OTf

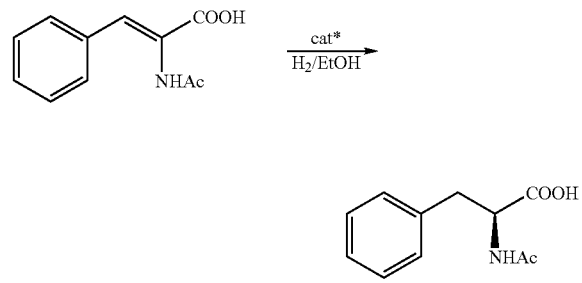

Experiment a

In a nitrogen atmosphere, 1.23 g (5.99 mmol) of N-acetamido cinnamic acid were dissolved in 100 mL of degassed EtOH, and 8.39 mg (0.012 mmol) of catalyst, prepared according to Example 5, were weighed in a nitrogen atmosphere.

The mixture was charged into a 250-mL autoclave under argon atmosphere. Three cycles of washing with Ar were then carried out. Then, the autoclave was cooled to 0÷2° C., then 3 cycles of washing with H$_2$ were carried out and the pressure was brought to 2 bar.

The reaction kinetic was followed by taking samples from the reaction mixture every 30 min.

The data obtained are reported in the following Table

| t (h) | Conv. (%) |
|---|---|
| 0.5 | 94 |
| 1 | 99.5 |

The enantiomeric excess of the product obtained N-acetylphenylalanine results equal to 98.9%.

Experiment b

Following the same experimental procedure described in the preceding experiment, with the sole difference consisting in the use of {Rh(COD) [1,2-bis (2R,5R)-2,5-dimethylphospholane)-benzene]} OTf (8 mg; 0.012 mmol) as catalyst the following kinetic results are obtained

| t (h) | Conv. (%) |
|---|---|
| 0.5 | 59 |
| 1 | 95.6 |
| 1.5 | 99.7 |

EXAMPLE 8

Hydrogenation of [6(R)]5,6-dihydro-4-hydroxy-3-[(Z)-1-(3-nitrophenyl) propenyl]-6-[1-(2-phenyl)ethyl]-6-propyl-2H-piran-2-one

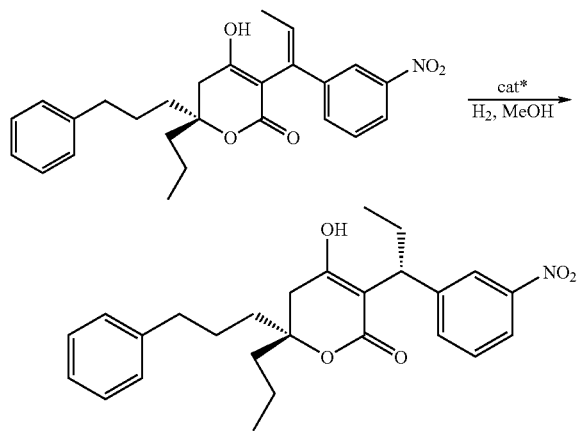

In a nitrogen atmosphere, 0.8 g (1.9 mmol) of [6(R)]5,6-dihydro-4-hydroxy-3-[(Z-1-(3-nitrophenyl)propenyl]-6-[1-(2-phenyl)ethyl]-propyl-2H-piran-2-one were dissolved in 100 mL of degassed MeOH, and 14 mg (0.019 mmol) of catalyst is prepared according to Example 5 were weighed under nitrogen.

The mixture was introduced into a 250-mL autoclave under argon atmosphere. Three cycles of washing with Ar were then carried out, followed by three cycles of washing With $H_2$. Then, the autoclave was pressurized at 5 bar.

The mixture was kept under stirring at room temperature for 20 hours. With this procedure, a 100% conversion was obtained, with a diastereoisomeric excess of [3 (R),6(R)]5,6-dihydro-4-hydroxy-3[1-(3-nitrophenyl)propyl]-6-[1-(2-phenyl)ethyl]-6-propyl-2H-piran-2-one corresponding to 91%.

EXAMPLE 9

Comparison of the Catalytic Activity of the Complex of the Present Invention (1b, 2b) with the known Complexes (1a, 2a) in Hydrogenation Reactions The catalyst utilised are reported in the following scheme 4.

Scheme 4

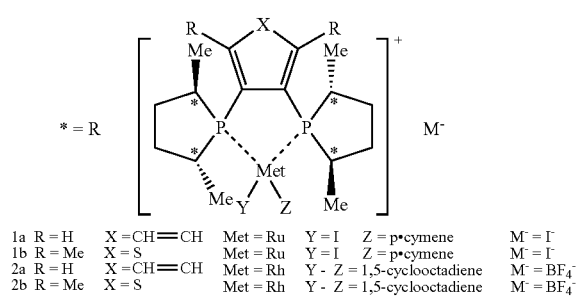

| | | | | | |
|---|---|---|---|---|---|
| 1a R = H | X = CH═CH | Met = Ru | Y = I | Z = p•cymene | M⁻ = I⁻ |
| 1b R = Me | X = S | Met = Ru | Y = I | Z = p•cymene | M⁻ = I⁻ |
| 2a R = H | X = CH═CH | Met = Rh | Y - Z = 1,5-cyclooctadiene | | M⁻ = BF₄⁻ |
| 2b R = Me | X = S | Met = Rh | Y - Z = 1,5-cyclooctadiene | | M⁻ = BF₄⁻ |

EXAMPLE 9A

Hydrogenation of N-Acetamidocinnamic Acid to N-Acetylphenylalanine

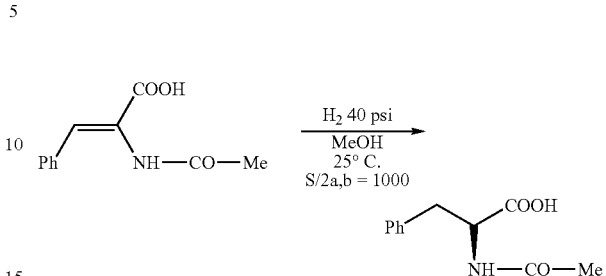

The hydrogenation of N-acetamidocinnamic acid to N-acetylphenylalanine was carried out at 40 psi hydrogen pressure, with 1000 as Substrate-(2a-b) catalyst molar ratio in methanol solution.

The reaction kinetics was found to be first order in the substrate in both cases, suggesting a common reaction mechanism, thus making the comparison of the data acceptable. Rate constants of $8.5 \times 10^{-3}$ and $1.1 \times 10^{-3}$ were determined for the reactions promoted by 2b and 2a respectively. These data add further proof of the strong influence exerted by the electronic availability at phosphorus of the ligand on kinetics. Electron-richer thiophene-based diphospholane fosters the reaction rate of nearly one order of magnitude with respect to the benzene-based one.

As expected on the basis of the geometries calculated for the ligands and their complexes, the enantioselection levels (hplc) were found nearly identical: 97.5 and 98.0% for the reactions promoted by 2b and 2a respectively.

EXAMPLE 9-B

Hydrogenation of ethyl acetoacetate to ethyl 3-hydroxybutirate

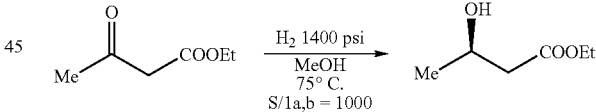

The hydrogenation of ethyl acetoacetate to ethyl 3-hydroxybutirate was carried out at 1400 psi hydrogen pressure, with 1000 as Substrate-(1a-b) Catalyst molar ratio in methanol solution, at 75° C. The progress of the reaction was monitored by gaschromatography.

Again, the kinetic behavior of the reactions using complexes 1a and 1b was found very similar. A rather prolonged induction period was observed in both cases, during which practically no reaction occurred. The induction time was longer when 1a was used (about 1100 min.) than when 1b was employed (about 700 min). Then the hydrogenation started displaying zero order kinetics in both cases. Rate constants of $3.7 \times 10^{-2}$ and $2.4 \times 10^{-2}$ were determined for the reactions promoted by 1b and 1a respectively. Once again electron-richer thiophene-based phospholane produced a more active promoter than the benzene-based one, whereas the enantiomeric excesses were almost the same 60 for the reaction carried out with the complex 1a versus 58% for 1b.

EXAMPLE 10

Synthesis of the Ligand (R,R)-2,5-dimethyl-3,4-bis[(2',5'-dimethyl)-phospholanyl]-1-phenylpyrrole Stage a: Synthesis of 2,5-dimethyl-3,4-bis(dibromophosphino)1-phenyl-pyrrole

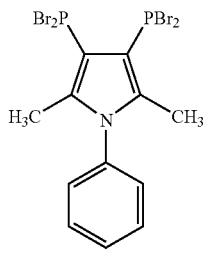

A solution of 2,5-dimethyl-1-phenylpyrrole (1.6 g, 9.4 mmol) (prepared as according to a procedure reported by A. Tolòmachev, S. P. Ivonin, A. A. Chaikovskaya, T. E. Terikovska, T. N. Kudrya, and A. M. Pinchuk *Heteroatom Chemistry*, 10, 1999, 223-229) in 10 mL of pyridine at 0° C. were slowly added to a solution of phosphorus tribromide (PBr$_3$) under stirring. After leaving the solution mixture under stirring for 17 hours at room temperature and under inert atmosphere, 25 mL hexane were added. The precipitate thus formed was removed from the reaction mixture by filtration and the solvent was removed from the filtrate by evaporation under reduced pressure. The residue was then washed three times with 20 mL of ethyl ether and dried under reduced pressure, thereby obtaining 3.36 g of the desired product (yield 36%).

$^1$H-NMR (CDCl$_3$): 2.2 (6H, s, 2 CH$_3$); 7.23-7.26 (2H, m, H$_{3,5}$-Ph); 7.54-7.57 (3H, m, H$_{2,4,6}$-Ph). $^{31}$P-NMR (CDCl$_3$): 130.2 (s).

Stage b: Synthesis of 3-(4-ethoxylhosphinoyl-1-phenyl-2,5-dimethyl)-pyrrolyl phosphinic acid ethyl ester

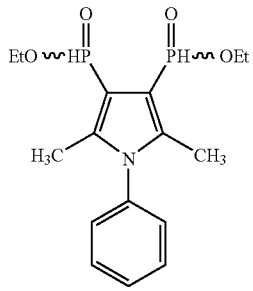

A solution of 2,5-dimethyl-3,4-bis(dibromophosphino)-1-phenyl-pyrrole prepared as described in step (a) (2.67 g, 4.85 mmol) was added to a stirred suspension of K$_2$CO$_3$ (2 g, 14.6 mmol) in ethanol (80 mL) and the mixture was left under stirring at room temperature for 10 hours. The solid was then filtered and the solvent was evaporated from the filtrate at reduced pressure, thereby obtaining 1.72 g of the desired product (quantitative yield).

$^1$H-NMR (CDCl$_3$): 1.43 (3H, t, J=7.06 Hz, OCH$_2$CH$_3$); 1.44 (3H, t, J=7.06 Hz, OCH$_2$CH$_3$); 2.25 (3H, d, J=1.42 Hz, CH$_3$); 2.29 (3H, d, J=1.46 Hz, CH$_3$); 4.13-4.26 (4H, m, OCH$_2$CH$_3$); 7.77 (1H, d, J$_{H-P}$=576.07 Hz, PH); 7.13-7.20 (2H, m, H$_{3,5}$-Ph); 7.50-7.63 (3H, m, H$_{2,4,6}$-Ph); 7.84 (1H, d, J$_{H-P}$=573.19 Hz, PH). $^{31}$P-NMR (CDCl$_3$): 18.8 (s); 23.3 (s). MASS: 355 (M$^+$); 337; 326; 309; 200 (100); 263; 234; 216; 201; 170.

Stage c: Synthesis of 2,5-dimethyl-3,4bis-(phosphino)1-phenyl-pyrrole

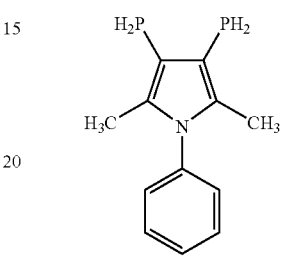

A solution of 3-(4-ethoxyphosphinoyl-1-phenyl-2,5-dimethyl)-pyrrolyl phosphinic acid ethyl ester prepared as described in step (c) (1 g, 1.82 mmol) in ethyl ether (85 mL) was added to a solution 1 M of LiAlH$_4$ in ethyl ether (6 mL) at 0° C., under stirring and under argon atmosphere. After leaving the reaction mixture for 1.5 h, 0.1 mL of 32% sodium hydroxide and anhydrous sodium sulfate. The reaction mixture was filtered and the solvent was removed by evaporation under reduced pressure thereby obtaining the desired product (400 mg yield 60%).

$^1$H-NMR (CDCl$_3$): 2.13 (6H, s, 2 CH$_3$); 3.66 (2H, d, J$_{H-P}$=206.89 Hz, PH$_2$); 7.14-7.17 (2H, m, H$_{3,5}$-Ph); 7.42-7.51 (3H; m, H$_{2,4,6}$-Ph). $^{31}$P-NMR (CDCl$_3$): −166.4 (t, J=1.68 Hz). MASS: 235 (M$^+$); 202; 171; 86.

Stage d: Synthesis of the Ligand (R,R)-2,5-dimethyl-3,4-bis[(2',5'-dimethyl)-phospholanyl]-1-phenylpyrrole

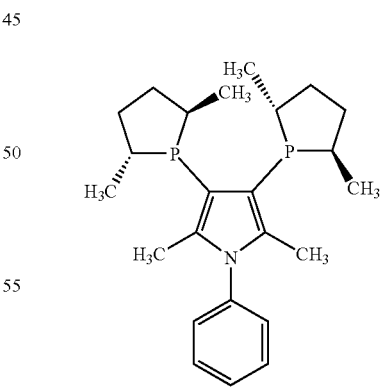

A solution of BuLi 1.6M in hexane (0.96 mL, 1.53 mmol) was dropped in a solution of 2,5-dimethyl-3,4bis-(phosphino)1-phenyl-pyrrole prepared as described in the previous stage (180 mg, 0.77 mmol) in THF (14.4 mL) and the reaction mixture was left under stirring for 1.5 h. 233 mg (1.53 mmol) of the cyclic sulfate of (2S,5S) hexanediol dissolved in 1.2 mL of THF were dropped in the reaction mixture, which was subsequently left under stirring for 1 h. The reaction mixture was quenched with methanol (0.3 mL) and the solvent evaporated under reduced pressure. The solid was then washed with n-heptane (3×20 mL) and the solvent was removed from the filtrate by evaporation under reduced pressure (20 torr), thereby obtaining the desired product (133 mg, yield 44%).

$[\alpha]_D = -17.4$, c=0.172, CHCl$_3$. $^1$H-NMR (CDCl$_3$): 0.93-0.99 (6H, m, CH$_3$); 1.16-1.26 (6H, m, CH$_3$); 1.62-1.77 (4H, m, —CH$_2$); 1.99-2.20 (4H, m, CH$_2$); 2.07 (6H, s, CH$_3$); 2.25-2.40 (2H, m, CHCH$_3$); 2.98-3.11 (2H, m, —CHCH$_3$); 7.12-7.20 (2H, m, H$_{3,5}$-Ph); 7.39-7.50 (3H, m, H$_{2,4,6}$-Ph). $^{31}$P-NMR (CDCl$_3$): −11.5 (s). MASS: 399 (M$^+$); 317; 202; 170. Electrochemical oxidation potential: 0.2 V.

The invention claimed:

1. A metallic catalyst of the formula (I)

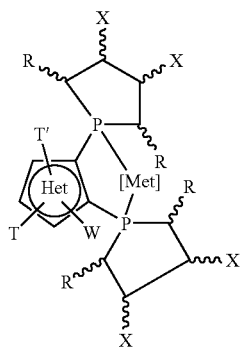

(I)

where:

[Met] is a metal selected from the group consisting of Ru, Rh, Ir, Pt, Pd, Ni, Re, and Cu, having a number of oxidation n, where n is 0, +1, +2 or +3, and containing possible ancillary co-ligands for completing its state of valence;

represents an aromatic pentatomic heterocycle, containing at least one hetero-atom selected from the group consisting of: oxygen, sulphur and nitrogen;

T and T', which are the same as or different from one another, are selected from the group consisting of hydrogen, a linear, cyclic or branched C1-C10 alkyl, hydroxyalkyl, alkoxyalkyl, phenyl, alkylphenyl, naphthyl, alkoxyphenyl, dialkylaminophenyl, carboxyphenyl, carbalkoxyphenyl, or else T and T', taken together, form an aromatic carbocyclic ring, possibly substituted by one or more alkyl, hydroxy, alkoxy, dialkylamino, carboxy, carbalkoxy or sulphonic groups;

W is a substituent present only when the hetero-atom is nitrogen and is selected from H, a linear, cyclic or branched C1-C10 alkyl, alkoxyalkyl, phenyl, alkylphenyl, naphthyl, alkoxyphenyl, dialkylaminophenyl, carboxyphenyl, carbalkoxyphenyl;

R is selected from hydrogen, a linear, cyclic or branched C1-C10 alkyl, hydroxyalkyl, alkoxyalkyl, phenyl, alkylphenyl;

X is selected from H, a linear, cyclic or branched C1-C10 alkyl, hydroxy, alkoxy, benzyloxy, acyloxy, O-tetrahydropyranyl, O-tetrahydrofuranyl, or else where the two substituents X, taken together with m carbon atoms bound thereto, with m=1, 2 or 3, form a carbocyclic ring with a total of 5-7 atoms or a saturated heterocyclic ring with 5-7 atoms.

2. The catalysts according to claim 1, wherein said catalyst is in racemic form.

3. The catalyst according to claim 1, wherein said catalyst is in meso form.

4. The catalysts according to claim 1, wherein said catalyst is in enantiomerically enriched form of configuration R or S with the limitation, that:
   a) the carbon atoms in positions 2' and 5' of the phospholanic rings possess the same absolute configuration with respect to one another;
   b) the carbon atoms in positions 3' and 4' of the phospholanic rings possess the same absolute configuration with respect to one another.

5. The catalyst, according to claim 1, of formula (V).

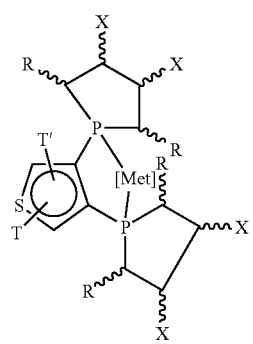

(V)

in which T, T', R, X and [Met] have the meanings indicated above.

6. The catalyst, according to claim 1, of formula (VI)

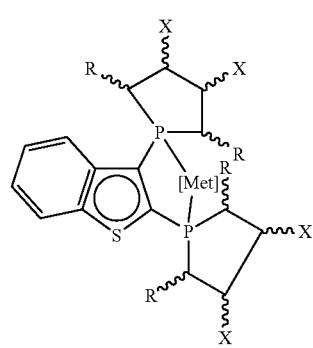

(VI)

in which R, X and [Met] have the meanings indicated above.

7. The catalyst according to claim 5, wherein T and T' are both H or both methyl.

8. The catalyst according to claim 5, selected from the group consisting of:

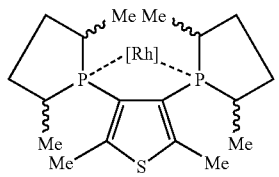

[Rh] = Rh(COD)BF$_4$

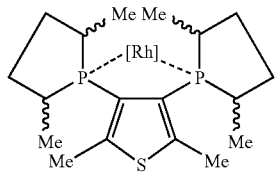

[Rh] = Rh(COD)OTf

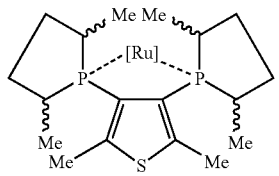

[Ru] = RuI(p•cimene)I

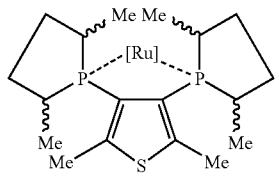

[Ru] = Ru(bis metallil)

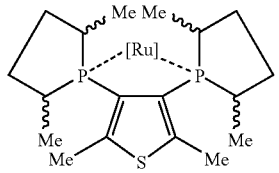

[Ru] = RuX$_2$

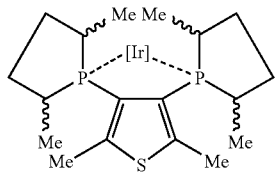

[Ir] = Ir(COD)OTf where the two stereocentres in positions 2' and 5' of the phospholanic rings have both absolute configuration (R) or both absolute configuration (S).

9. The catalyst according to to claim 1 of formula (VII)

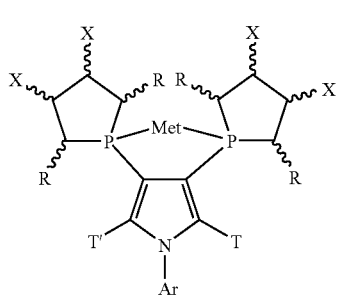

(VII)

wherein T and T' are both H or both the same linear, cyclic or branched C1-C10 alkyl, R is CH$_3$, Ar is an electron donor arylic residue.

10. The catalyst according to claim 9 having the following formula

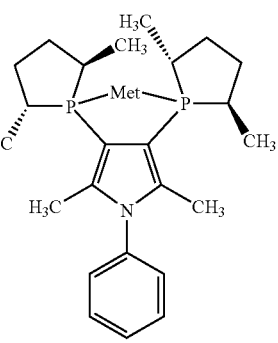

wherein Met has the aforesaid meanings.

11. A ligand with an ortho bis(1-phospholanyl)heteroarenic structure of formula (IA)

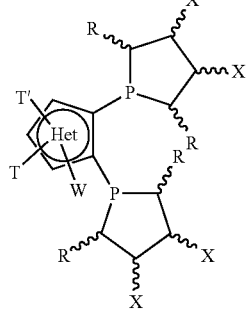

(IA)

in which

represents an aromatic pentatomic heterocycle, containing at least one hetero-atom selected from the group consisting of oxygen, sulphur and nitrogen;

T and T', which are the same as or different from one another, are selected from hydrogen, a linear, cyclic or branched C1-C10 alkyl, hydroxyalkyl, alkoxyalkyl, phenyl, alkylphenyl, naphthyl, alkoxyphenyl, dialkylaminophenyl, carboxyphenyl, carbalkoxyphenyl, or else T and T' taken together form an aromatic carbocyclic ring possibly substituted by one or more alkyl, hydroxy, alkoxy, dialkylamino, carboxy, carbalkoxy or sulphonic groups;

W is a substituent present only when the hetero-atom is nitrogen and is selected from H, a linear, cyclic or branched C1-C10 alkyl, alkoxyalkyl, phenyl, alkylphenyl, naphthyl, alkoxyphenyl, dialkylaminophenyl, carboxyphenyl, carbalkoxyphenyl;

R is selected from hydrogen, a linear, cyclic or branched C1-C10 alkyl, hydroxyalkyl, alkoxyalkyl, phenyl, alkylphenyl;

X is selected from H, a linear, cyclic or branched C1-C10 alkyl, hydroxy, alkoxy, benzyloxy, acyloxy, O-tetrahydropyranyl, O-tetrahydrofuranyl, or else where the two substituents X, taken together with m carbon atoms bound thereto, with m=1, 2 or 3, form a carbocyclic ring with a total of 5-7 atoms or a saturated heterocyclic ring with 5-7 atoms.

12. The ligand according to claim 11, wherein said ligand is in racemic form.

13. The ligand according to claim 11, wherein said ligand is in meso form.

14. The ligand according to claim 11, wherein said ligand is in enantiomerically enriched form of configuration R or S with the limitation, that:
   a) the carbon atoms in positions 2' and 5' of the phospholanic rings possess the same absolute configuration with respect to one another;
   b) the carbon atoms in positions 3' and 4' of the phospholanic rings possess the same absolute configuration with respect to one another.

15. The ligand according to claim 11, wherein said ligand has the following formula (II)

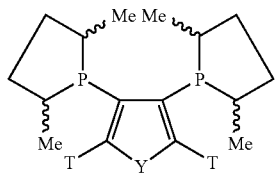

(II)

and in which Y is selected from O, S and N(W), T and W are selected from hydrogen and methyl, and where the carbon atoms in positions 2' and 5' of the phospholanic rings have both absolute configuration (R) or both absolute configuration (S).

16. The ligand according to claim 11, wherein said ligand has the following formula (III)

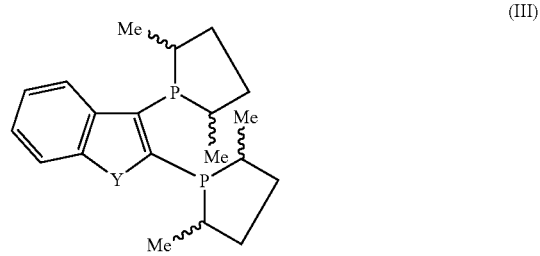

(III)

in which Y is selected from O, S and N(W), T and W are selected from hydrogen and methyl, and where the carbon atoms in positions 2' and 5' of the phospholanic rings have both absolute configuration (R) or both absolute configuration (S).

17. The ligand according to claim 11, wherein said ligand has the following formula (IV)

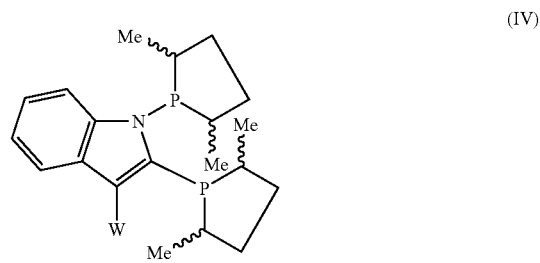

(IV)

and in which W is selected from hydrogen and methyl and where the carbon atoms in positions 2' and 5' of the phospholanic rings have both absolute configuration (R) or both absolute configuration (S).

18. The ligand according to claim 11 wherein said ligand has the following general formula (VIIA)

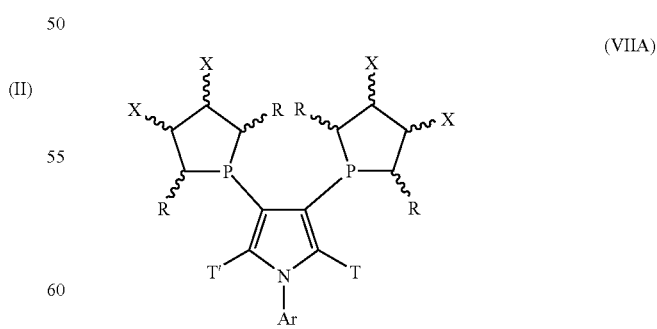

(VIIA)

wherein T and T' preferably are both H or both the same linear, cyclic or branched C1-C10 alkyl, R is $CH_3$, Ar is an electron donor aryl residue.

19. The ligand according to claim 18 wherein said ligand has the following formula

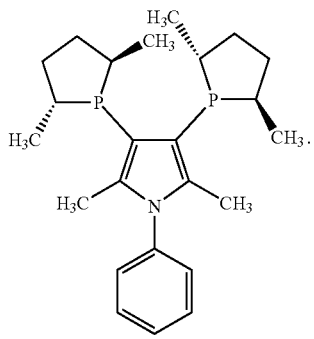

20. A process of preparation of the catalyst according to claim 1 comprising the reaction of [Met] in which [Met] has the aforesaid meanings, with a ligand with an ortho bis(1-phospholanyl)heteroarenic structure of the formula (IA)

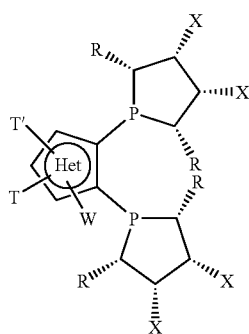 (IA)

in which

represents an aromatic pentatomic heterocycle, containing at least one hetero-atom selected from the group consisting of oxygen, sulphur and nitrogen;

T and T', which are the same as or different from one another, are selected from hydrogen, a linear, cyclic or branched C1-C10 alkyl, hydroxyalkyl, alkoxyalkyl, phenyl, alkylphenyl, naphthyl, alkoxyphenyl, dialkylaminophenyl, carboxyphenyl, carbalkoxyphenyl, or else T and T' taken toaether form an aromatic carbocyclic ring possibly substituted by one or more alkyl, hydroxyl, alkoxy, diakylamino, carboxy, carbalkoxy or sulphonic groups;

W is a substituent present only when the hetero-atom is nitrogen and is selected from H, a linear, cyclic or branched C1-C10 alkyl, alkoxyalkyl, phenyl, alkylphenyl, naphthyl, alkoxyphenyl, dialkylaminophenyl, carboxyohenyl, carbalkoxyphenyl;

R is selected from hydrogen, a linear, cyclic or branched C1-C10 alkyl, hydroxyalkyl, alkoxyalkyl, phenyl, alkylphenyl;

X is selected from H, a linear, cyclic or branched C1-C10 alkyl, hydroxy, alkoxy, benzyloxy, acyloxy, O-tetrahydropyranyl, O-tetrahydrofuranyl, or else where the two substituents X, taken together with m carbon atoms bound thereto, with m=1, 2 or 3, form a carbocyclic ring with a total of 5-7 atoms or a saturated heterocyclic ring with 5-7 atoms.

21. The catalyst according to claim 1 for use in chemoselective syntheses.

22. The catalyst according to claim 1 for use in a regioselective syntheses.

23. The catalyst according to claim 1 for use in a stereoselective syntheses.

24. The catalyst according to claim 4 for use in stereoselective syntheses.

25. The catalyst according to claim 23, wherein said stereoselective syntheses are selected from the group consisting of:

hydrogenation of C=C, C=O, C=N groups isomerization of enamines and formation of C—C bonds.

26. The catalyst according to claim 24, wherein said stereoselective syntheses are selected from the group consisting of:

hydrogenation of C=C, C=O, C=N groups isomerization of enamines and formation of C—C bonds.

27. The catalyst according to claim 25, wherein said formation of C—C bonds are selected from the group consisting of the Heck reaction, the Diels-Alder reaction, allylic substitution and aldolic condensation.

28. The catalyst according to claim 26, wherein said formation of C—C bonds are selected from the group consisting of the Heck reaction, the Diels-Alder reaction, allylic substitution and aldolic condensation.

* * * * *

UNITED STATES PATENT AND TRADEMARK OFFICE
CERTIFICATE OF CORRECTION

PATENT NO. : 7,307,037 B2 Page 1 of 2
APPLICATION NO. : 10/506305
DATED : December 11, 2007
INVENTOR(S) : Sannicolo et al.

It is certified that error appears in the above-identified patent and that said Letters Patent is hereby corrected as shown below:

Column 7, delete

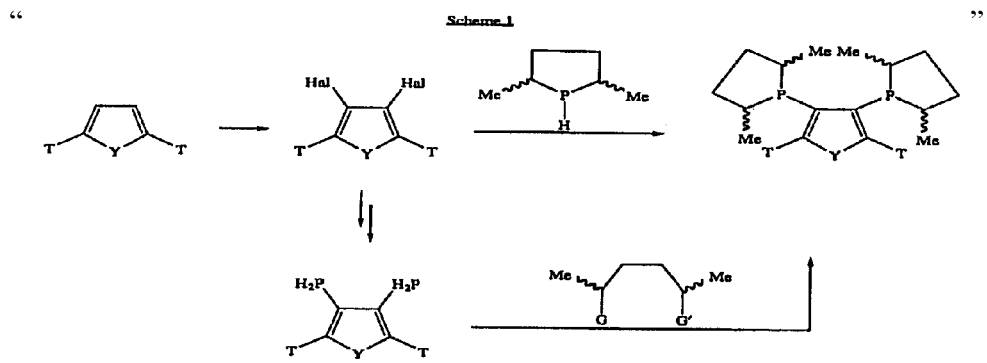

replace with --

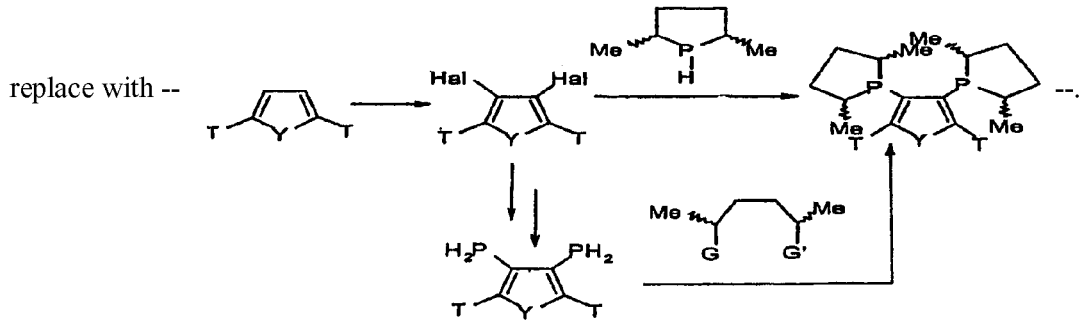

Column 18, Line 29, replace "at," with --at--.

Column 19, Line 36, replace "vacuum Approximately" with --vacuum. Approximately--.

Column 26, Line 12, replace "catalysts" with --catalyst--.

UNITED STATES PATENT AND TRADEMARK OFFICE
CERTIFICATE OF CORRECTION

PATENT NO. : 7,307,037 B2
APPLICATION NO. : 10/506305
DATED : December 11, 2007
INVENTOR(S) : Sannicolo et al.

It is certified that error appears in the above-identified patent and that said Letters Patent is hereby corrected as shown below:

Column 31, Line 25, delete

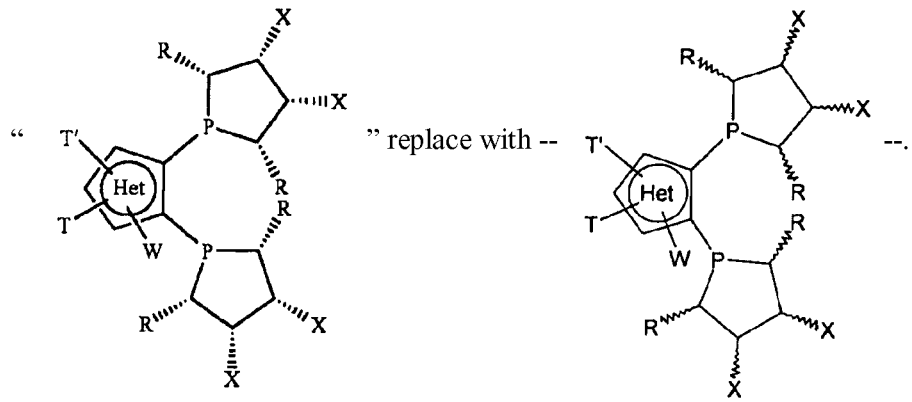

Column 32, Line 6, replace "hydroxyl" with --hydroxy--.

Column 32, Line 6, replace "diakylamino" with --dialkylamino--.

Column 32, Lines 11-12, replace "carboxyohenyl" with --carboxyphenyl--.

Signed and Sealed this

Sixth Day of January, 2009

JON W. DUDAS
*Director of the United States Patent and Trademark Office*